United States Patent [19]

Chu et al.

[11] Patent Number: 5,789,591

[45] Date of Patent: Aug. 4, 1998

[54] PROCESS FOR PREPARING 1-SUBSTITUTED 8-CHLORO-7-FLUORO-9-METHYL-4-OXO-4H-QUINOLIZINE-3-CARBOXYLIC ACID ETHYL ESTER COMPOUNDS

[75] Inventors: Daniel T. Chu, Santa Clara, Calif.; David Allen Degoey, Kenosha, Wis.; David J. Grampovnik, Waukegan, Ill.; Larry Lewis Klein, Lake Forest, Ill.; Paul A. Lartey, Wadsworth, Ill.; Christina Louise Leone, Kenosha, Wis.; Sheela Albert Thomas, Vernon Hills, India; Ming Clinton Yeung, Grayslake, Ill.

[73] Assignee: Abbott Laboratories, Abbott Park, Ill.

[21] Appl. No.: 735,625

[22] Filed: Oct. 23, 1996

[51] Int. Cl.⁶ .................................................. C07D 455/02
[52] U.S. Cl. ..................................................................... 546/138
[58] Field of Search ...................................................... 546/138

[56] References Cited

FOREIGN PATENT DOCUMENTS

WO 95/10519  4/1995  WIPO .

OTHER PUBLICATIONS

Caine, D., "Alkylations of Enols and Enolates", *Alkylation of Carbon*, University of Alabama, Tuscaloosa, AL, pp. 1–63, 1991.

Stork, G., et al., "Alkylations of Aldehydes vai Reaction of the Magnesioneamine Salt of an Aldehyde: 2,2-Dimethyl-3-Phenylpropionaldehyde", *Organic Syntheses*, vol. 54, pp. 46–49, 1974.

Stork, G., et al., "A New Method for the Alkylation of Ketones and Aldehydes: the C–Alkylation of the Magnesium Salts of N–Substituted Imines", Communication to the Editor, vol. 85, Jul. 20, 1963, pp. 2178–2180.

Whitsell, J., et al., "Alkylation of Ketones and Aldehydes via their Nitrogen Derivatives", *Synthesis*, Jul. 1983, pp. 517–536.

Mar. J. *Advanced Organic Chemistry: Reactions, Mechanisms, and Structure*, 4th edition, p. 470, Jun. 1993.

*Primary Examiner*—John Kight
*Assistant Examiner*—Garth M. Dahlen
*Attorney, Agent, or Firm*—Mona Anand

[57] ABSTRACT

A process for preparing a compound having the formula:

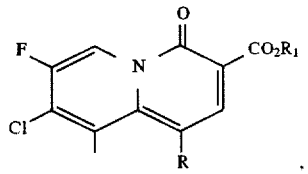

wherein R is selected from the group consisting of $C_3$–$C_6$-cycloalkyl, $C_3$–$C_6$-cycloalkylmethyl, $C_1$–$C_6$-alkyl, allyl and 2-methoxyethyl, by reacting:

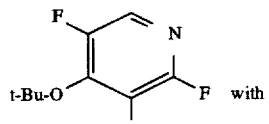

with

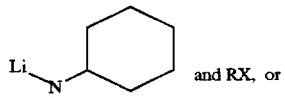 and RX, or

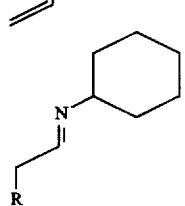

under defined conditions with subsequent stepwise reactions of the respective intermediate compounds with a malonic acid diester, $POCl_3$, and by heating the final intermediate in a high boiling solvent.

8 Claims, No Drawings

PROCESS FOR PREPARING 1-SUBSTITUTED 8-CHLORO-7-FLUORO-9-METHYL-4-OXO-4H-QUINOLIZINE-3-CARBOXYLIC ACID ETHYL ESTER COMPOUNDS

FIELD OF THE INVENTION

The present invention relates to a process for preparing compounds having use as intermediates in the preparation of antimicrobial agents.

BACKGROUND OF THE INVENTION

4-Oxo-4H-quinolizine-3-carboxylic acid compounds represented by formula:

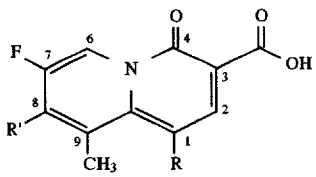

are described in PCT applications WO 91/16894, published Nov. 14, 1991, and WO 95/10519 published Apr. 20, 1995. These compounds are known to be highly effective antimicrobial agents having activity against a wide spectrum of Gram-positive and Gram-negative bacteria as well as enterobacteria.

The synthesis of a key intermediate necessary for the preparation of the 1-substituted-4-oxo-4H-quinolizine-3-carboxylic acid compounds having the formula:

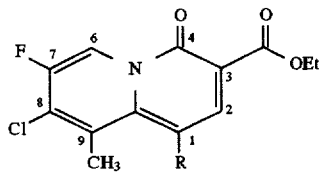

is described in the applications cited above, and requires nine steps. An improved and more efficient method of preparation of this and analogous compounds would be desirable for availability of antibiotic preparations derived therefrom.

It is known to alkylate imine anions to obtain α-alkylated carbonyl compounds which can used as intermediates in the synthesis of more complex molecules. Whitesell and Whitesell, *Synthesis*, 1983:517; Cainelli, et al., *Pure Appl. Chem.*, 62:605 (1990); and Caine, et al., *Comprehensive Organic Synthesis* 3:1, (1991) describe reactions with imine anions. However, none of these references discloses the use of imine anions in one of the key steps in the preparation of 4-oxo-4H-quinolizine-3-carboxylic acid compounds.

SUMMARY OF THE INVENTION

It has been found that the use of imine anion in the preparation of the various substituted 4-oxo-4H-quinolizine-3-carboxylic acid compounds provides an efficient process which is three steps shorter than the nine-step process described in PCT applications WO 91/16894, published Nov. 14, 1991, and WO 95/10519, published Apr. 20, 1995.

The present invention provides a process for preparing 1-substituted-8-chloro-7-fluoro-9-methyl-4-oxo-4H-quinolizine-3-carboxylic acid ester compounds represented by the formula (I):

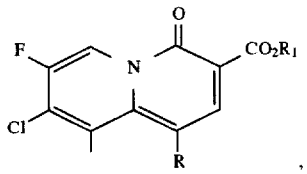

wherein R is selected from the group consisting of:

(a) $C_3-C_6$-cycloalkyl;
(b) $C_3-C_6$-cycloalkylmethyl;
(c) $C_1-C_6$-alkyl;
(d) allyl; and
(e) 2-methoxyethyl; and $R_1$ is $C_1-C_6$-alkyl or arylalkyl; the method comprising:

(1) reacting 4-t-butoxy-3-methyl-2,5-difluoropyridine, having the formula:

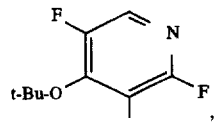

with a compound having the structure:

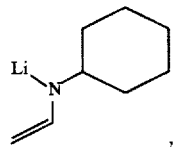

followed by reaction with a compound having the formula R-X, wherein X is chloro, bromo or iodo and R is selected from the group consisting of:

(a) $C_3-C_6$-cycloalkyl;
(b) $C_3-C_6$-cycloalkylmethyl;
(c) $C_1-C_6$-alkyl;
(d) allyl; and
(e) 2-methoxyethyl;

and isolating the first intermediate compound having the formula:

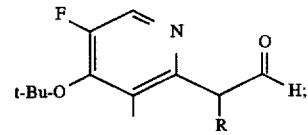

(2) reacting the first intermediate compound with a malonic acid diester and isolating the second intermediate compound having the formula:

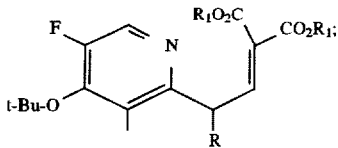

(3) reacting the second intermediate compound with POCl$_3$, and isolating the third intermediate compound having the formula:

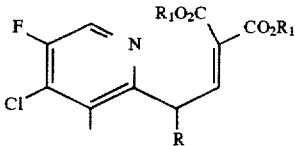

(4) heating the third intermediate compound in a solvent, and isolating the desired product.

In another embodiment of the process, the process comprises:

(1) reacting 4-t-butoxy-3-methyl-2,5-difluoropyridine, having the formula:

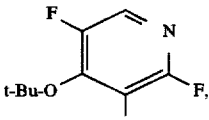

with a Schiff base compound having the formula:

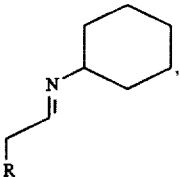

wherein R is selected from the group consisting of:
(a) $C_3$–$C_6$-cycloalkyl;
(b) $C_3$–$C_6$-cycloalkylmethyl;
(c) $C_1$–$C_6$-alkyl;
(d) allyl; and
(e) 2-methoxyethyl;

in the presence of alkali metal base, and isolating the first intermediate compound having the formula:

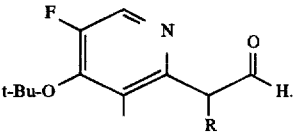

The subsequent steps (2), (3) and (4) of the process are the same as described above.

DETAILED DESCRIPTION OF THE INVENTION

The term "$C_1$–$C_6$-alkyl" refers to saturated, straight- or branched-chain hydrocarbon radicals containing between one and six carbon atoms including, but not limited to, methyl, ethyl, propyl, isopropyl, n-butyl, tert-butyl and neopentyl.

The term "arylalkyl" refers to a $C_1$–$C_6$-alkyl radical having appended thereto an aromatic hydrocarbon group, as for example benzyl and phenylethyl.

The term "$C_3$–$C_6$-cycloalkyl" refers to a saturated monocyclic hydrocarbon radical having from three to six carbon atoms in the ring. Examples of cycloalkyl radicals include, cyclopropyl, cyclobutyl, cyclopentyl, and cyclohexyl.

The term "aprotic solvent" or "aprotic organic solvent", as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

"Aprotic polar solvents" are those aprotic solvents, as defined above, that possess a significant dipole moment (cf Riddick, op. cit.), and include tetrahydrofuran, dimethylformamide, N-methylpyrrolidinone, diethyl ether, bis-methoxymethyl ether, dioxane, and the like.

The term "high boiling solvent" refers to a solvent possessing a boiling point above 100° C., preferably in the range of 100° C. to 250° C. Illustrative of, but not limited to, high-boiling solvents include DMF, DMSO, diethoxyethane, biphenyl ether and diphenyl ether, or mixtures thereof, for example, 30% biphenyl ether and 70% diphenyl ether, which is commercially available under the name Dowtherm A™.

The process of the invention may be better understood by reference to the reaction schemes illustrated below. Abbreviations which have been used in the descriptions of the scheme and the examples that follow are: DIBAL for diisobutylaluminum hydride; DMF for dimethylformamide; DMSO for dimethyl sulfoxide; LDA for lithium diisopropylamide; DMPU for 1,3-dimethyl-3,4,5,6-tetrahydro-2(1H)-pyrimidone; THF for tetrahydrofuran.

Scheme 1

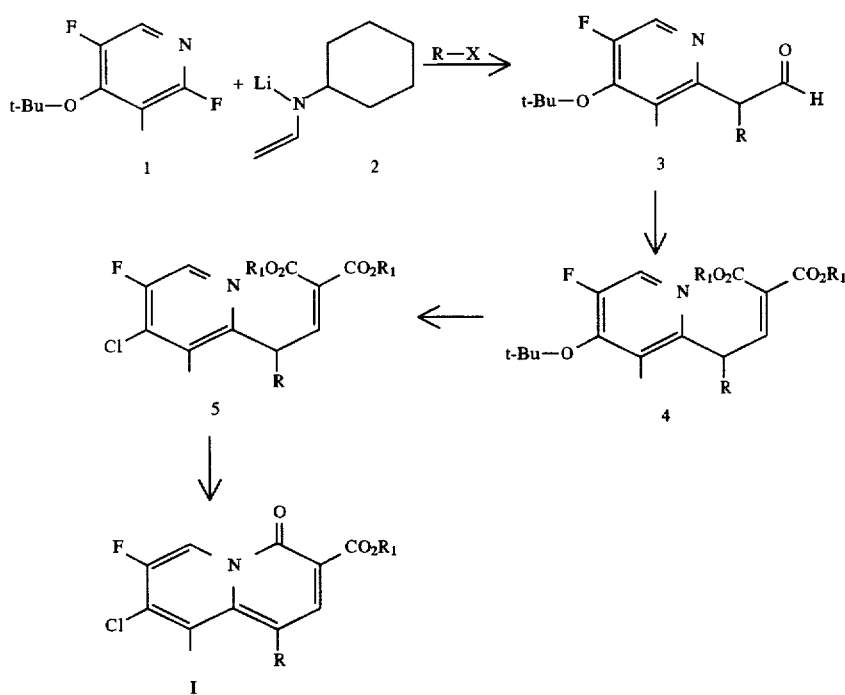

One embodiment of the process of the invention is illustrated in Scheme 1. The 4-t-butoxy-2,5-difluoro-3-methylpyridine compound (1) (prepared by the method described in PCT application WO 91/16894, published Nov. 14, 1991) is reacted with the lithium salt of N-(ethylidene)-cyclohexylamine (2). N-(ethylidene)-cyclohexylamine is prepared by reacting acetaldehyde with cyclohexylamine, and the Li salt thereof is prepared by treating the imine with a lithium base, for example, LDA, lithium diisopropylamide or lithium hexamethyldisilazide, at from −20° C. to ambient temperature. The preparation of compound (2) is carried out most easily in solution in an aprotic polar organic solvent, and the reaction may be carried out at from −20° C. to ambient temperature.

When the starting fluoropyridine (1) has fully reacted with compound (2), the resulting intermediate is reacted with the desired R-X compound, wherein X is chloro, bromo or iodo and R is selected from the group consisting of $C_3$–$C_6$-cycloalkyl, $C_3$–$C_6$-cycloalkylmethyl, $C_1$–$C_6$-alkyl, allyl and 2-methoxyethyl. This latter reaction may be carried out most easily by addition of RX to the same reaction vessel to prepare the compound (3). Depending upon the R and X moieties chosen, the reaction may be exothermic and thus carried out at ambient temperature or may be accomplished with stirring for from 1 to 24 hours at an elevated temperature, for example, from 30° C. to 80° C. After quenching the reaction and isolation of the product (3), it may be taken directly to the next step or may be purified as necessary by chromatography, for example.

The aldehyde compound (3) is then reacted with a malonic acid diester, such as diethyl malonate, dibenzyl malonate, t-butyl malonate or di-t-butyl malonate, followed by isolation of the intermediate compounds of formula (4). This reaction may be performed in a polar solvent, such as ethanol, methanol, is-propanol, butanol or dioxane, for example, and may be accelerated and yields improved by the addition of a weak organic base, such as triethylamine, piperidine or pyridine, for example, and a catalytic amount of an acid, such as acetic acid or sulfuric acid. This reaction may be performed at a temperature of from ambient to 80° C. for from 4 to 24 hours.

The compounds of formula (4) are then reacted with $POCl_3$ in an aprotic organic solvent, to prepare the compounds of formula (5). The reaction may be cooled or performed at ambient temperature and may require 4 to 24 hours for completion. Compound (5) is then heated in a solvent to form the 4-oxo-4H-quinolizine-3-carboxylic acid ethyl ester compounds of formula (I). This reaction is preferably carried out at a temperature of from 100° C. to 250° C. in a high-boiling solvent, so that the ethanol by-product may be removed easily. The reaction may require from 0.5 to 24 hours for completion.

Another embodiment of the process is illustrated in Scheme 2 below.

Scheme 2

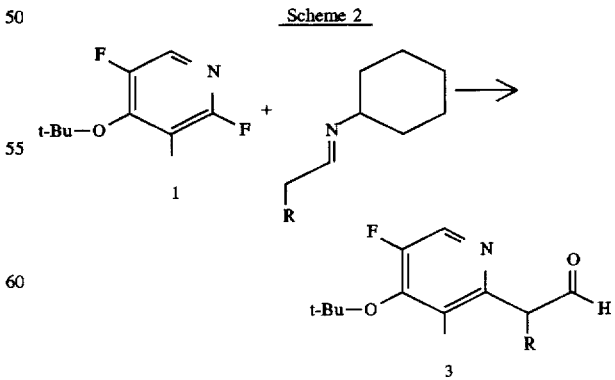

The Schiff base compound having the formula (8) in Scheme 2 may be prepared as shown in Scheme 3 below.

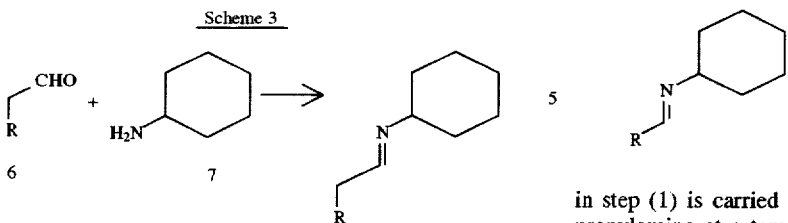

Scheme 3

An aldehyde compound having the formula (6), wherein R is selected from the group consisting of $C_3$-$C_6$-cycloalkyl, $C_3$-$C_6$-cycloalkylmethyl, $C_1$-$C_6$-alkyl, allyl and 2-methoxyethyl, is reacted with cyclohexylamine (7) in the presence of a base, for example $K_2CO_3$, under well-known and standard conditions for preparing Schiff bases.

In accordance with Scheme 2, compounds (3) are alternately prepared by reaction of compound (1) with an N-(alkylidene)cyclohexylamine compound (8), wherein R is selected from the group consisting of $C_3$-$C_6$-cycloalkyl, $C_3$-$C_6$-cycloalkylmethyl, $C_1$-$C_6$-alkyl, allyl and 2-methoxyethyl in the presence of an alkali metal base, preferably with a lithium base, for example, LDA, lithium diisopropylamide or lithium hexamethyldisilazide. The N-(alkylidene)cyclohexylamine (8) is prepared by reacting the appropriate aldehyde, R-CHO, wherein R is as described above, with cyclohexylamine. The preparation of compound (3) is carried out most easily in solution in an aprotic polar organic solvent, and the reaction may be carried out at from −20° C. to ambient temperature. This reaction is carried out most easily in solution, using THF or another aprotic polar organic solvent. The subsequent conversion of compound (3) to compound (I) may be accomplished by following the procedures described in steps (2), (3) and (4) in Scheme 1.

In a preferred embodiment of the process of the invention, in step (1) the reaction with:

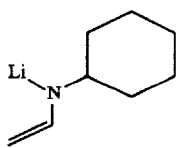

is carried out at a temperature of from 0° C. to ambient for from 1 to 24 hours, followed by reaction in the same vessel at ambient or an elevated temperature with the compound having the formula R-X. The first intermediate (3) is reacted with diethyl malonate at a temperature of from ambient to 80° C. for from 4 to 24 hours. In step (3) the reaction is performed with dimethylformamide with cooling or at ambient temperature for 4 to 24 hours; and in step (4) the reaction is performed at a temperature of from 100° C. to 250° C. for from 4 to 24 hours in a mixture of biphenyl and diphenyl ethers.

In a more preferred embodiment of the process of the invention, R in formula (I) is cyclopropyl.

In a preferred embodiment of the alternate process of the invention illustrated in Scheme 2, the reaction with:

in step (1) is carried out in the presence of lithium diisopropylamine at a temperature of from −20° C. to ambient temperature. The first intermediate (3) is reacted with diethyl malonate in step (2) at a temperature of from ambient to 80° C. for from 4 to 24 hours. In step (3), the reaction is performed with dimethylformamide with cooling or at ambient temperature for 4 to 24 hours; and in step (4) the reaction is performed at a temperature of from 100° C. to 250° C. for from 4 to 24 hours in a mixture of biphenyl and diphenyl ethers.

In a more preferred embodiment of the alternate process of the invention, R in formula (I) is cyclopropyl.

The 1-substituted-8-chloro-7-fluoro-9-methyl-4-oxo-4H-quinolizine-3-carboxylic acid ethyl ester compounds prepared herein may be employed as intermediates in the preparation of suitably 8- and 1-substituted-7-fluoro-9-methyl-4-oxo-4H-quinolizine-3-carboxylic acid ethyl ester antibiotic agents.

The preferred 1-cyclopropyl-8-chloro-7-fluoro-9-methyl-4-oxo-4H-quinolizine-3-carboxylic acid ethyl ester compound prepared herein may be employed as an intermediate in the preparation of suitably 8-substituted 1-cyclopropyl-7-fluoro-9-methyl-4-oxo-4H-quinolizine-3-carboxylic acid ethyl ester antibiotic agents.

EXAMPLES

The invention may be better understood by reference to the following examples, which are provided for the illustration and are not limitation of the invention.

Example 1

Reference Preparation of 8-chloro-1-cyclopropyl-7-fluoro-9-methyl-4-oxo-4H-quinolizine-3-carboxylic acid ethyl ester Step 1a. 4-t-Butoxy-3-chloro-2,5,6-trifluoropyridine To 250 mL of a THF solution containing 106 g (0.571 mmol) of a mixture of 4-chloro-tetrafluoropyridine and 3-chloro-tetrahydropyridine (approximately 70:30 ratio, from Aldrich Chemical Co.) at −78° C. was added a solution of 38.3 g (0.399 mmol) of sodium t-butoxide in 350 mL of THF, and the solution was stirred for 2 hours at −78° C. and at ambient temperature for 16 hours. The mixture was poured into 500 mL of hexane, and this mixture was filtered through celite and the filtrate concentrated. The residue was purified by flash chromatography, eluting first with hexane, then ethyl acetate:hexane (1:4), to separate the desired title product from the mixture of products. MS 238, 240 (M+H)$^+$; 1H NMR (CDCl$_3$) ∂: 1.52 (d, J=2Hz); $^{19}$F NMR (CDCl$_3$, CFCl$_3$ as reference) ∂: 73.75 (dd, J$_1$=14.2, J$_2$=23.2 Hz), 89.71 (dd, J$_1$=14.2, J$_2$=21.98 Hz); 152.42 (apparent t, J=22 Hz).

Step 1b. 4-t-Butoxy-2,3,6-trifluoropyridine

To the product from Step 1a above (24.92 g, 0.104 mmol) in 100 mL of methanol was added 2.5 g of Pearlman's catalyst (Aldrich Chemical Co.), and the mixture was stirred at ambient temperature for 14 hours under and atmosphere of hydrogen. An additional 2.5 g of catalyst was added, and the mixture was stirred for another 22 hours. The mixture was filtered, the filtrate was concentrated, and the residue was extracted with hexane/ether. After filtration, the solvent was removed by evaporation, and the residue was purified by flash chromatography (ethyl acetate:hexane 1:16) to yield 12.05 g of the title product. MS 206 (M+H)$^+$, 233 (M+18)$^+$; 1H NMR (CDCl$_3$) ∂: 1.52 (s, 9H), 6.51 (m, 1H); $^{19}$F NMR (CDCl$_3$, CFCl$_3$ as reference) ∂: 72.60 (dd, J$_1$=14.3, J$_2$=21.0 Hz), 89.74 (dd, J$_1$=14.3, J$_2$=21.0 Hz), 164.68 (dt, J$_1$=4.2, J$_2$=21.0 Hz).

Step 1c. 4-t-Butoxy-2,3,6-trifluoro-5-methylpyridine

A freshly prepared solution of lithium diethylamide (LDA) (58.21 mmol) in 30 mL of THF at –78° C. was added to 10.0 g (48.74 mmol) of the product from Step 1b in 50 mL of THF at –78° C., and the reaction was stirred for 50 minutes. To the reaction mixture was added 4.3 mL (69.07 mmol) of methyl iodide, and the mixture was stirred at –78° C. for 1 hour and stirred at ambient temperature for 16 hours. The reaction was quenched with saturated NH$_4$Cl solution, extracted with hexane, and the extracts washed with water, dried over MgSO$_4$ and concentrated to give the title product as a pale yellow oil, which was taken directly to the next step. MS (220) (M+H)$^+$; 1H NMR (CDCl$_3$) ∂: 1.47 (m, 9H), 2.12 (m, 3H). $^{19}$F NMR (CDCl$_3$, CFCl$_3$ as reference) ∂: 75.91 (dd apparent, J$_1$=15.0, J$_2$=22.1 Hz), 93.17 (dd apparent, J$_1$=15.0, J$_2$=22.1 Hz), 156.54 (m).

Step 1d. 4-t-Butoxy-2,5-difluoro-3-methylpyridine

A sample of the product from Step 1c above (48.74 mmol) and 13.5 mL of hydrazine monohydrate were dissolved in 150 mL of n-propanol. The reaction was stirred at reflux temperature under nitrogen for 4 hours. The volatiles were removed, and the residue was dissolved in methylene chloride, which was washed with water and dried over MgSO$_4$. The solvent was removed to give the intermediate hydrazine product as a yellow liquid, which was dissolved in 110 mL of methanol. To this was added 20 mL of 20% NaOH and air was passed through the solution for 16 hours. The solvents were removed at 30° C. under vacuum. The residue was dissolved in methylene chloride, which was washed with water and dried over MgSO$_4$. The solvent was removed and the crude product purified by flash chromatography, eluting with ethyl acetate:hexane 1: 16 to give the title product as a colorless liquid after removal of the solvents. MS (202) (M+H)$^+$; 1H NMR (CDCl$_3$) ∂: 1.43 (d, 9H, J=1.5 Hz), 2.18 (d, 3H, J=1.5 Hz), 7.85 (br s, 1H); $^{19}$F NMR (CDCl$_3$, CFCl$_3$ as reference) ∂: 73.37 (d, J=24.5 Hz), 142.17 (d, J=24.5 Hz).

Step 1e. 2-(4-t-Butoxy-5-fluoro-3-methyl-2-pyridinyl) cyclopropaneacetonitrile

A sample of the product from Step 1d above (40.8 mmol) was dissolved in 50 mL of THF and cooled to –78° C. To this was added a freshly prepared solution of LDA (0.103 mmol) in 50 mL of THF at –78° C., and the reaction was stirred for 1 hour. The reaction was then stirred at 0° C. for 1 hour, quenched with saturated NH$_4$Cl solution and extracted with ether. The extracts were washed with saturated NaCl solution, dried over MgSO$_4$, and concentrated. The residue was purified by flash chromatography, eluting with 1:4 ethyl acetate:hexane, to yield 10.33 g of the title product after removal of the solvent MS 263 (M+H)$^+$; 1H NMR (CDCl$_3$) ∂: 0.50 (m, 2H), 0.63 (m, 1H), 0.73 (m, 1H), 1.60 (m, 1H), 1.43 (d, 9H, J=2 Hz), 2.29 (s, 3H), 3.76 (d, 1H, J=8 Hz), 8.30 (d, 1H, J=3 Hz). IR (neat) 2240, 1580, 1470 cm$^{-1}$.

Step 1f. 2-(4-Chloro-5-fluoro-3-methyl-2-pyridinyl) cyclopropaneacetonitrile

A sample of the product from Step 1e above (5.21 g, 19.86 mmol) was dissolved in 50 mL of trifluoroacetic acid, the reaction was stirred under nitrogen for 1 hour at ambient temperature, and the material concentrated to dryness. The residue was dissolved in a mixture of 15.6 mL of DMF and 90 mL of methylene chloride. This solution was cooled in a water bath as 18.8 mL (19.86 mmol) of POCl$_3$ was added, then the reaction was stirred at ambient temperature for 16 hours. The reaction was quenched by pouring it into ice water, and the mixture was extracted with methylene chloride. The aqueous solution was adjusted to pH7 with NaOH and re-extracted with methylene chloride. The extracts were combined and washed with water, dried over MgSO$_4$ and concentrated. The residue was purified by flash chromatography with 1:4 ethyl acetate:hexane to give 3.26 g of the title product as a colorless liquid after removal of the solvents. MS 225, 227 (M+H)$^+$; 1H NMR (CDCl$_3$) ∂: 0.48 (m, 1H), 0.59 (m, 1H), 0.66 (m, 1H), 0.77 (m, 1H), 1.50 (m, 1H), 2.48 (s, 3H), 3.80 (d, 1H, J=8 Hz), 8.39 (s, 1H). IR (neat) 2240, 1570, 1460 cm$^{-1}$.

Step 1g. Ethyl 2-(4-chloro-5-fluoro-3-methyl-2-pyridinyl) cyclopropaneacetate

A sample of the product from Step 1f above (3.26 g, 14.51 mmol) was dissolved in 10 mL of ethanol, and gaseous HCl was introduced until 4 g had been dissolved. The solution was heated to reflux, and 0.36 mL of water was added, then the mixture was stirred for 1 hour. The reaction was cooled, then poured into water, and the mixture was adjusted to pH7 with NaHCO$_3$. The mixture was then extracted with methylene chloride, which was washed with water, dried over MgSO$_4$ and concentrated. The residue was triturated with 1:4 ethyl acetate:hexane, and filtered. The filtrate was concentrated and the residue was purified by flash chromatography with 1:4 ethyl acetate:hexane to give 2.262 g of the title product after removal of the solvent. MS 272, 274 (M+H)$^+$; 1 H NMR (CDCl$_3$) ∂: 0.12 (m, 1H), 0.38 (m, 1H), 0.53 (m, 1H), 0.76 (m, 1H), 1.20 (t, 3H, J=7 Hz), 1.67 (m, 1H), 2.40 (s, 3H), 3.23 (d, 1H, J=9 Hz), 4.16 (q, 2H, J=7 Hz), 8.36 (s, 1H).

Step 1h. 2-(4-Chloro-5-fluoro-3-methyl-2-pyridinyl) cyclopropaneacetaldehyde

A sample of the product from Step 1g above (1.73 g, 6.37 mmol) was dissolved in 10 mL of THF and stirred with water bath cooling and 3.2 mmol of LiAlH$_4$ (LAH) was added. The mixture was stirred at ambient temperature for 1 hour, then poured into water. This mixture was extracted with ether, the extracts were washed, dried and concentrated to give 1.48 g of a colorless oil. This oil was dissolved in 10 mL of methylene chloride and added to a solution of 3.8 mL (7.6 mmol) of oxalyl chloride and 1.1 mL of DMSO (15.5 mmol) in 15 mL of methylene chloride stirred at –78° C. The solution was stirred for 15 min, and 4.4 mL (31.6 mmol) of triethylamine was added. The stirring was continued at –78° C. for 5 min and at –10° C. for 10 minutes. The reaction was quenched with water, and extracted with methylene chloride. The extract was washed, dried and concentrated to give 1.49 g of the crude title product, which was taken directly to the next step without further purification. MS 228, 230 (M+H)$^+$; 1H NMR (CDCl$_3$) ∂: 0.25 (m, 1H), 0.35 (m, 1H), 0.60 (m, 1H), 0.75 (m, 1H), 1.53 (m, 1H), 2.38 (s, 3H), 3.19 (dd, 1H, J=3, J=9 Hz), 8.37 (s, 1H), 9.86 (d, 1H, J=3 Hz).

Step 1i. 8-Chloro-1-cyclopropyl-7-fluoro-9-methyl-4-oxo-4H-quinolizine-3-carboxylic acid ethyl ester A sample of the product from Step 1h above (6.37 mmol) was dissolved in 50 mL of ethanol, and to this were added 1.5 mL of piperidine, 1.5 mL of acetic acid, and 5 mL of diethyl malonate (32.9 mmol). The reaction was heated at reflux under nitrogen for 4 hours. The solvents were then removed, and the residue was dissolved in ether. The ether was washed with water and brine, then dried over MgSO$_4$ and concentrated. Purification in a kugelrohr apparatus gave 2.4 g of the crude condensation product. This intermediate product was dissolved in 20 mL of Dowtherm A™, and this solution was added to 100 mL of Dowtherm A™ heated to 235° C. The reaction was then stirred at 220° C. for 45 minutes. After cooling, the product was separated from the solvent by flash chromatography, eluting with hexane to remove the solvent and then with 1:4 ethyl acetate hexane to remove the product. In this manner 1.065 g of the title product was obtained after removal of the solvent. MS 324, 326 (M+H)$^+$; 1H NMR (CDCl$_3$) ∂: 0.75 (m, 2H), 1.07 (m, 2H), 1.42 (t, 3H, J=7 Hz), 2.31 (m, 1H), 3.08 (s, 3H), 4.42 (q, 2H, J=7 Hz), 8.40 (s, 1H), 9.44 (d, 1H, J=6 Hz).

Example 2

8-Chloro- 1-methyl-7-fluoro-9-methyl-4-oxo-4H-quinolizine-3-carboxylic acid ethyl ester 2a. 2-(4-t-Butoxy-5-fluoro-3-methyl-2-pyridinyl) propionaldehyde To a solution of LDA (6.22 mmol, prepared from diisopropylamine (0.81 mL) and n-BuLi (2.5M in hexanes, 2.49 mL) in THF (5.0 mL) at 0° C. was added N-(propylidene)-cyclohexylamine (0.89 mL, 6.47 mmol, prepared in situ from propionaldehyde and cyclohexylamine) dropwise, and the reaction mixture was stirred for 20 minutes. To this solution at 0° C. was added DMPU (6.22 mmol), the mixture was stirred for 10 minutes, then cooled to −78° C. To this solution was added 4-t-butoxy-5-fluoro-3-methylpyridine (0.50 mL, 2.49 mmol) dropwise, and the mixture was warmed to −20° C. and stirred at this temperature for 16 hours. The reaction was then quenched with acetic acid (1M, 15 mL), diluted with hexanes (100 mL) and dilute acetic acid (1M, 85 mL), and stirred vigorously for 1 hour. The organic layer was separated, washed with water, dried (MgSO$_4$) and concentrated. The residue was purified by chromatography on silica gel, eluting with 5% to 10% ethyl acetate in hexanes, to afford the title compound (0.24 g, 49% yield) as an oil. MS 240 (M+H)$^+$; 1H NMR (CDCl$_3$) δ1.43 (d, 3H, J=7.0 Hz), 1.43 (d, 9H, J=1.1 Hz), 2.26 (s, 3H), 3.84 (q, 1H, J =7.0 Hz), 8.26 (d, 1H, J=2.2 Hz), 9.78 (d, 1H, J=1.1 Hz).

2b. 4-(4-t-butoxy-5-fluoro-3-methyl-2-pyridinyl)-2-ethoxycarbonyl-2-propenoic acid ethyl ester To a solution of 2-(4-t-butoxy-5-fluoro-3-methyl-2-pyridinyl)propionaldehyde (from step 2a, 0.66 g, 2.76 mmol) dissolved in ethanol (15 mL) was added piperidine (0.60 mL, 6.07 mmol), acetic acid (0.60 mL, 10.49 mmol) and diethyl malonate (1.90 mL, 12.53 mmol), and the mixture was heated at reflux for 16 hours. After cooling, the mixture was extracted with ether, which was washed with water, saturated NaHCO$_3$ and brine, dried over MgSO$_4$ and concentrated. The residue was purified by chromatography on silica gel, eluting with 5% to 10% ethyl acetate in hexanes, to afford the title compound (0.86 g, 82% yield) as an oil. The product is a 1:1 mixture of two isomeric olefins. MS 382 (M+H)$^+$; 1H NMR (CDCl$_3$) δ1.20–1.31 (m, 12H), 1.43–1.44 (m, 18H), 2.06 (s, 3H), 2.06 (s, 3H), 2.11 (s, 3H), 2.24 (s, 3H), 3.66 (d, 1H, J=9.9 Hz), 4.08–4.27 (m, 8H), 4.44 (d, 1H, J=9.6 Hz), 5.70–5.74 (m, 1H), 5.87–5.91 (m, 1H), 8.23 (d, 1H, J=2.2 Hz), 8.28 (d, 1H, J=2.6 Hz).

2c. 4-(4-chloro-5-fluoro-3-methyl-2-pyridinyl)-2-ethoxycarbonyl-2-propenoic acid ethyl ester To a solution of 4-(4-t-butoxy-5-fluoro-3-methyl-2-pyridinyl)-2-ethoxycarbonyl-2-propenoic acid ethyl ester (from step 2b, 0.70 g, 1.84 mmol) in methylene chloride (7 mL) and DMF (0.71 mL, 9.19 mmol) at 0° C., POCl$_3$ (0.86 mL, 9.19 mmol) was added dropwise. The mixture was warmed to room temperature and stirred for 23 hours. The reaction was quenched with ice, and the mixture was extracted with ether. The organic layer was washed with water, saturated NaHCO$_3$ and brine, dried over MgSO$_4$ and concentrated. The residue was purified by chromatography on silica gel, eluting with 10% to 20% ethyl acetate in hexanes, to afford the title compound (0.57 g, 90% yield) as an oil. The product is a 1:1 mixture of two isomeric olefins. MS 344, 346 (M+H)$^+$; 1H NMR (CDCl$_3$) δ1.18–1.34 (m, 12H), 2.07 (m, 6H), 2.28 (s, 3H), 2.42 (s, 3H), 3.65 (d, 1H, J=9.9 Hz), 4.05–4.29 (m, 8H), 4.43 (d, 1H, J=9.2 Hz), 5.71–5.77 (m, 1H), 5.93–5.99 (m, 1H), 8.31 (s, 1H), 8.36 (s, 1H).

2d. 8-Chloro-1-methyl-7-fluoro-9-methyl-4-oxo-4H-quinolizine-3-carboxylic acid ethyl ester Following the procedure of Example 1i, substituting the 4-(4-chloro-5-fluoro-3-methyl-2-pyridinyl)-2-ethoxycarbonyl-2-propenoic acid ethyl ester from step 2c for the compound from step 1h, the title compound was prepared (69% yield). MS 298, 300 (M+H)$^+$; 1H NMR (CDCl$_3$) δ1.43 (t, 3H, J=7.0 Hz), 2.70 (s, 3H), 2.87 (s, 3H), 4.42 (q, 2H, J=7.0 Hz), 8.23 (s, 1H), 9.44 (d, 1H, J=5.5 Hz).

Example 3

8-Chloro- 1 -cyclopropyl-7-fluoro-9-methyl-4-oxo-4H-quinolizine-3-carboxylic acid ethyl ester 3a. N-(2-cyclopropylethylidene)cyclohexylamine To a solution of cyclopropylacetonitrile (7.0 ml, 82 mmol) in 200 ml of methylene chloride/hexanes (1:1) at −78° C. was added 90.0 ml of 1M DIBAL in hexanes (90 mmol) dropwise over 20 minutes. After complete addition, the solution was warmed to 0° C. and stirred for 2 hours. At this time, 140 ml of ethyl acetate was added at 0° C. and the solution warmed to room temperature. To the solution was added 140 ml of saturated NH$_4$Cl and 250 ml of 1N H$_2$SO$_4$. The mixture was diluted with ether and shaken vigorously until the organic layer became clear. The organic layer was then washed with saturated NaHCO$_3$. To this crude aldehyde solution was added 55 g of K$_2$CO$_3$ and 9.4 ml of cyclohexylamine (82 mmol) at room temperature and the reaction stirred for 48 hours. The reaction was filtered and evaporated and the residue distilled under reduced pressure to give the title compound. MS 166 (M+H)$^+$; 1H NMR (CDCl$_3$) δ0.12–0.19 (m, 2H), 0.46–0.53 (m, 2H), 0.76–0.91 (m, 1H), 0.95–1.90 (m, 10H), 2.12 (dd, 2H, J=5.2 Hz, J=7.4 Hz), 2.93 (m, 1H), 7.71 (t, 1H, J=5.1 Hz).

3b. 2-(4-t-Butoxy-5-fluoro-3-methyl-2-pyridinyl)-2-cyclopropylacetaldehyde

To a solution of LDA (1.20 mmol, prepared from diisopropylamine (0.16 mL) and n-BuLi (2.5M in hexanes, 0.48 mL) in THF (2.0 mL) at 0° C. was added N-(2-cyclopropylethylidene)cyclohexylamine (1.24 mmol, from step 3a) dropwise, and the reaction mixture was warmed to room temperature and stirred for 15 minutes. To this solution was added 4-t-butoxy-5-fluoro-3-methylpyridine (0.10 mL, 0.50 mmol) in THF (0.5 mL) dropwise and the mixture was stirred for 3.5 hours. The reaction was then quenched with acetic acid (1M, 3 mL), diluted with hexanes (20 mL) and dilute acetic acid (1M, 20 mL), and stirred vigorously for 1 hour. The organic layer was separated, washed with water, saturated NaHCO$_3$ and brine, dried (MgSO$_4$) and concentrated. The residue was purified by chromatography on silica gel, eluting with 5% to 15% ethyl acetate in hexanes, to afford the title compound (0.098 g, 75% yield) as an oil. MS 266 (M+H)$^+$; 1H NMR (CDCl$_3$) δ0.19–0.32 (m, 2H), 0.52–0.75 (m, 2H), 1.42 (d, 9H, J=1.1 Hz), 1.42–1.60 (m, 1H), 2.20 (s, 3H), 3.16 (dd, 1H, J=2.6 Hz, J =8.8 Hz), 8.29 (d, 1H, J=2.2 Hz), 9.86 (d, 1H, J=2.6 Hz).

3c. 8-Chloro-1-cyclopropyl-7-fluoro-9-methyl-4-oxo-4H-quinolizine-3-carboxylic acid ethyl ester Following the procedures of Example 2, steps b–d, except substituting the 2-(4-t-butoxy-5-fluoro-3-methyl-2-pyridinyl)-2-cyclopropylacetaldehyde from step 3a for the 2-(4-t-butoxy-5-fluoro-3-methyl-2-pyridinyl)propionaldehyde of step 2b, the title compound was prepared. MS 324, 326 (M+H)$^+$; 1H NMR (CDCl$_3$) $\partial$: 0.75 (m, 2H), 1.07 (m, 2H), 1.42 (t, 3H, J=7 Hz), 2.31 (m, 1H), 3.08 (s, 3H), 4.42 (q, 2H, J=7 Hz), 8.40 (s, 1H), 9.44 (d, 1H, J=6 Hz).

Example 4

1-Allyl-8-chloro-7-fluoro-9-methyl-4-oxo-4H-quinolizine-3-carboxylic acid ethyl ester 4a. 2-allyl-2-(4-t-Butoxy-5-fluoro-3-methyl-2-pyridinyl)-acetaldehyde To a solution of LDA (1.75 mmol, prepared from diisopropylamine (0.23 mL) and n-BuLi (2.5 M in hexanes, 0.70 mL) in THF (2.0 mL) at 0° C. was added N-(ethylidene)-cyclohexylamine (1.70 mmol, prepared in situ from acetaldehyde and cyclohexylamine) dropwise, and the reaction mixture was warmed to room temperature and stirred for 15 minutes. To this solution was added 4-t-butoxy-5-fluoro-3-methylpyridine (0.10 mL, 0.50 mmol) in THF (0.5 mL) dropwise and the mixture was stirred for 1 hour. To this mixture was added allyl bromide (0.15 mL, 1.75 mmol) dropwise.. The exothermic reaction was stirred for 20 minutes, then quenched with water (3 mL). The mixture was then diluted with acetic acid (1M, 20 mL) and hexanes (20 mL) and stirred vigorously for 1 hour. The mixture was extracted with ether, and the organic layer was separated, washed with water, saturated NaHCO$_3$ and brine, dried (MgSO$_4$) and concentrated. The residue was purified by chromatography on silica gel, eluting with 5% to 10% ethyl acetate in hexanes, to afford the title compound (0.095 g, 73% yield) as an oil. MS 266 (M+H)$^+$; 1H NMR (CDCl$_3$) $\delta$1.41 (d, 9H, J=1.1 Hz), 2.25 (s, 3H), 2.55–2.67 (m, 1H), 2.81–2.93 (m, 1H), 3.85 (m, 1H), 4.93–5.04 (m, 2H), 5.65–5.80 (m, 1H), 8.27 (d, 1H, J=1.8 Hz), 9.74 (m, 1H).

4b. 1-Allyl-8-chloro-7-fluoro-9-methyl-4-oxo-4H-quinolizine-3-carboxylic acid ethyl ester Following the procedures of Example 2, steps b–d, except substituting the 2-allyl-2-(4-t-butoxy-5-fluoro-3-methyl-2-pyridinyl)acetaldehyde from step 4a for the 2-(4-t-butoxy-5-fluoro-3-methyl-2-pyridinyl)propionaldehyde of step 2b, the title compound was prepared. MS 324, 326 (M+H)$^+$; 1H NMR (CDCl$_3$) $\delta$1.43 (t, 3H, J=7.0 Hz), 2.82 (s, 3H), 3.71–3.73 (m, 2H), 4.43 (q, 2H, J=7 Hz), 4.86–4.95 (m, 1H), 5.12–5.28 (m, 1H), 6.02–6.16 (m, 1H), 8.23 (s, 1H), 9.47 (d, 1H, J=6.3 Hz).

Example 5

8-Chloro-1-isopropyl-7-fluoro-9-methyl-4-oxo-4H-quinolizine-3-carboxylic acid ethyl ester 5a. 2-(4-t-Butoxy-5-fluoro-3-methyl-2-pyridinyl)-2-(3-methyl)butyraldehyde To a solution of LDA (1.75 mmol, prepared from diisopropylamine (0.23 mL) and n-BuLi (2.5M in hexanes, 0.70 mL) in THF (2.0 mL) at 0° C. was added N-(ethylidene)-cyclohexylamine (1.70 mmol, prepared in situ from acetaldehyde and cyclohexylamine) dropwise, and the reaction mixture was warmed to room temperature and stirred for 15 minutes. To this solution was added 4-t-butoxy-5-fluoro-3-methylpyridine (0.10 mL, 0.50 mmol) in THF (0.5 mL) dropwise and the mixture was stirred for 1 hour. To this mixture was added isopropyl iodide (0.18 mL, 1.75 mmol) dropwise. The reaction was heated at reflux for 12 hours, then quenched with water (3 mL). The mixture was then diluted with acetic acid (1M, 20 mL) and hexanes (20 mL) and stirred vigorously for 1 hour. The mixture was extracted with ether, and the organic layer was separated, washed with water, saturated NaHCO$_3$ and brine, dried (MgSO$_4$) and concentrated. The residue was purified by chromatography on silica gel, eluting with 5% to 10% ethyl acetate in hexanes, to afford the title compound (0.13 g, 99% yield) as an oil. MS 268 (M+H)$^+$; 1H NMR (CDCl$_3$) $\delta$0.75 (d, 3H, J=6.6 Hz), 1.05 (d, 3H, J=6.6 Hz), 1.41 (d, 9H, J=1.1 Hz), 2.24 (s, 3H), 2.58–2.72 (m, 1H), 3.41 (dd, 1H, J=4.4 Hz, J=9.9 Hz), 8.31 (d, 1H, J=2.2 Hz), 9.75 (d, 1H, J=4.4 Hz).

5b. 8-Chloro-1-isopropyl-7-fluoro-9-methyl-4-oxo-4H-quinolizine-3-carboxylic acid ethyl ester Following the procedures of Example 2, steps b–d, except substituting the 2-(4-t-butoxy-5-fluoro-3-methyl-2-pyridinyl)-2-(3-methyl)butyraldehyde from step 5a for the 2-(4-t-butoxy-5-fluoro-3-methyl-2-pyridinyl)propionaldehyde of step 2b, the title compound was prepared. MS 326, 328 (M+H)$^+$; 1H NMR (CDCl$_3$) $\delta$1.33 (d, 3H, J=6.6 Hz), 1.44 (t, 3H, J=7.0 Hz), 1.56 (s, 3H), 2.79 (s, 3H), 3.53–3.64 (m, 1H), 4.44 (q, 2H, J=7.0 Hz), 8.46 (s, 1H), 9.40 (d, 1H, J=6 Hz).

Example 6

8-Chloro-1-cyclopropylmethyl-7-fluoro-9-methyl-4-oxo-4H-quinolizine-3-carboxylic acid ethyl ester Following the procedures of Example 2, except substituting cyclopropylmethyl bromide for the isopropyl iodide of step 5a, the title compound was prepared (73% yield). MS 338, 340 (M+H)$^+$; 1H NMR (CDCl$_3$) $\delta$0.21–0.29 (m, 2H), 0.57–0.66 (m, 2H), 0.88–1.02 (m, 1H), 1.43 (t, 3H, J=7.0 Hz), 2.89 (s, 3H), 2.96 (d, 2H, J=6.3 Hz), 4.43 (q, 2H, J=7.0 Hz), 8.46 (s, 1H), 9.47 (d, 1H, J=5.5 Hz).

Example 7

8-Chloro-1-(2-methoxyethyl)-7-fluoro-9-methyl-4-oxo-4H-guinolizine-3-carboxylic acid ethyl ester Following the procedures of Example 2, except substituting 2-methoxyethyl bromide for the isopropyl iodide of step 5a, the title compound was prepared (75% yield). MS 342, 344 (M+H)$^+$; 1H NMR (CDCl$_3$) $\delta$1.43 (t, 3H, J=7.0 Hz), 2.87 (s, 3H), 3.27 (t, 2H, J=7.0 Hz), 3.35 (s, 3H), 3.61 (t, 2H, J=7.0 Hz), 4.43 (q, 2H, J=7.0 Hz), 8.31 (s, 1H), 9.45 (d, 1H, J=5.9 Hz).

Example 8

8-Chloro-1-(2,2-dimethylpropyl)-7-fluoro-9-methyl-4-oxo-4H-quinolizine-3-carboxylic acid ethyl ester Following the procedures of Example 2, except substituting 2,2-dimethylpropyl iodide for the isopropyl iodide of step 5a, the title compound was prepared (91% yield). MS 354, 356 (M+H)$^+$; 1H NMR (CDCl$_3$) $\delta$0.76 (s, 9H), 1.42 (t, 3H, J=7.0 Hz), 2.78 (s, 3H), 2.99 (s, 2H), 4.42 (q, 2H, J=7.0 Hz), 8.21 (s, 1H), 9.43 (d, 1H, J=5.5 Hz).

Example 9

8-Chloro-1-cyclopentyl-7-fluoro-9-methyl-4-oxo-4H-quinolizine-3-carboxylic acid ethyl ester Following the procedures of Example 2, except substituting cyclopentyl bromide for the isopropyl iodide of step 5a, the title compound was prepared (100% yield). MS 352, 354 (M+H)⁺; 1H NMR (CDCl₃) δ1.43 (t, 3H, J=7.0 Hz), 1.59–2.15 (m, 8H), 2.78 (s, 3H), 3.42–3.55 (m, 1H), 4.43 (q, 2H, J=7.0 Hz), 8.44 (s, 1H), 9.37 (d, 1H, J=5.5 Hz).

Example 10

8-Chloro-1-(2-methylpropyl)-7-fluoro-9-methyl-4-oxo-4H-quinolizine-3-carboxylic acid ethyl ester Following the procedures of Example 2, except substituting 2-butyl iodide for the isopropyl iodide of step 5a, the title compound was prepared (88% yield). MS 340, 342 (M+H)⁺; 1H NMR (CDCl₃) δ0.77 (t, 3H, J=7.4 Hz), 1.36 (d, 3H, J=6.6 Hz), 1.44 (t, 3H, J=7.0 Hz), 1.64 (m, 2H), 2.77 (s, 3H), 3.27 (q, 1H, J=7 Hz), 4.43 (q, 2H, J=7.0 Hz), 8.40 (s, 1H), 9.40 (d, 1H, J=5.5 Hz).

What is claimed is:

1. A process for preparing 1-substituted-8-chloro-7-fluoro-9-methyl-4-oxo-4H-quinolizine-3-carboxylic acid ethyl ester compounds having the formula:

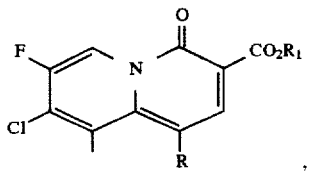

(I), wherein R is selected from the group consisting of:
(a) $C_3$–$C_6$-cycloalkyl;
(b) $C_3$–$C_6$-cycloalkylmethyl;
(c) $C_1$–$C_6$-alkyl;
(d) allyl; and
(e) 2-methoxyethyl; and $R_1$ is $C_1$–$C_6$-alkyl or arylalkyl;
the method comprising:
(1) reacting 4-t-butoxy-3-methyl-2,5-difluoropyridine, having the formula:

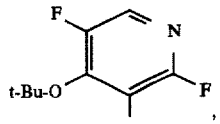

with a compound having the structure:

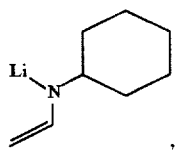

followed by reaction with a compound having the formula R-X, wherein X is chloro, bromo or iodo and R is selected from the group consisting of:
(a) $C_3$–$C_6$-cycloalkyl;
(b) $C_3$–$C_6$-cycloalkylmethyl;
(c) $C_1$–$C_6$-alkyl;
(d) allyl; and
(e) 2-methoxyethyl;

and isolating the first intermediate compound having the formula:

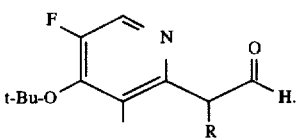

(2) reacting the first intermediate compound with a malonic acid diester and isolating the second intermediate compound having the formula:

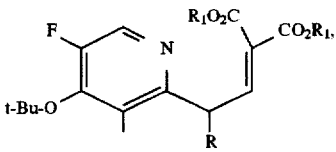

(3) reacting the second intermediate compound with POCl₃, and isolating the third intermediate compound having the formula:

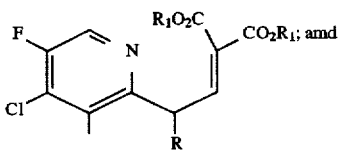

(4) heating the third intermediate compound in a high-boiling solvent, and isolating the desired product.

2. A process according to claim 1 wherein R in formula (I) is cyclopropyl.

3. A process according to claim 1, comprising:

(1) carrying out reaction with:

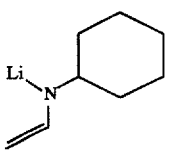

at a temperature of from 0° C. to ambient for from 1 to 24 hours, followed by reaction at ambient or an elevated temperature with the compound having the formula R-X;

(2) reacting the first intermediate with diethyl malonate at a temperature of from ambient to 80° C. for from 4 to 24 hours;

(3) reacting the second intermediate with dimethylformamide with cooling or at ambient temperature for 4 to 24 hours; and (4) heating the third intermediate at a temperature of from 100° C. to 250° C. for from 4 to 24 hours in a mixture of biphenyl and diphenyl ethers.

4. A process according to claim 3 wherein R in formula (I) is cyclopropyl.

5. A process for preparing 1-substituted-8-chloro-7-fluoro-9-methyl-4-oxo-4H-quinolizine-3-carboxylic acid ethyl ester compounds having the formula:

17

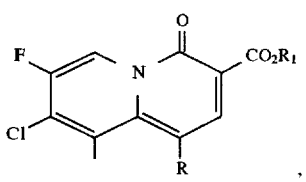

wherein R is selected from the group consisting of:
(a) $C_3$–$C_6$-cycloalkyl;
(b) $C_3$–$C_6$-cycloalkylmethyl;
(c) $C_1$–$C_6$-alkyl;
(d) allyl; and
(e) 2-methoxyethyl; and $R_1$ is $C_1$–$C_6$-alkyl or arylalkyl;
the method comprising
(1) reacting 4-t-butoxy-3-methyl-2,5-difluoropyridine, having the formula:

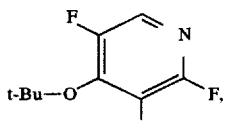

with a Schiff base compound having the formula:

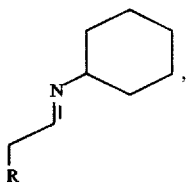

wherein R is selected from the group consisting of
(a) $C_3$–$C_6$-cycloalkyl;
(b) $C_3$–$C_6$-cycloalkylmethyl;
(c) $C_1$–$C_6$-alkyl;
(d) allyl; and
(e) 2-methoxyethyl;
in the presence of an alkali metal base, and isolating the first intermediate compound having the formula:

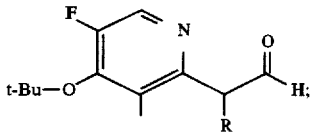

(2) reacting the first intermediate compound with a malonic acid diester and isolating the second intermediate compound having the formula:

18

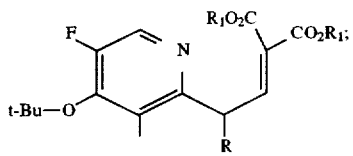

(3) reacting the second intermediate compound with $POCl_3$, and isolating the third intermediate compound having the formula:

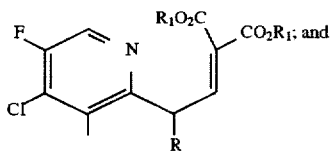

(4) heating the third intermediate compound in a high-boiling solvent, and isolating the desired product.

6. A process according to claim 5 wherein R in formula (I) is cyclopropyl.

7. A process according to claim 5 comprising:
(1) carrying out reaction with:

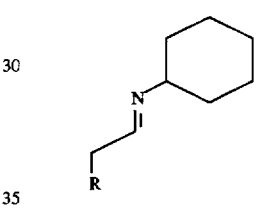

at a temperature of from 0° C. to ambient for from 1 to 24 hours, followed by reaction in the same vessel at ambient or an elevated temperature with the compound having the formula R-X;

(2) reacting the first intermediate with diethyl malonate at a temperature of from ambient to 80° C. for from 4 to 24 hours;

(3) reacting the second intermediate with dimethylformamide with cooling or at ambient temperature for 4 to 24 hours; and (4) heating the third intermediate at a temperature of from 100° C. to 250° C. for from 4 to 24 hours in a mixture of biphenyl and diphenyl ethers.

8. A process according to claim 7 wherein R in formula (1) is cyclopropyl.

* * * * *

UNITED STATES PATENT AND TRADEMARK OFFICE
CERTIFICATE OF CORRECTION

PATENT NO. : 5,789,591
DATED : August 4, 1998
INVENTOR(S) : Chu et al.

It is certified that error appears in the above-identified patent and that said Letters Patent is hereby corrected as shown below:

Title page, inventors section, change "India" to --Ill.;--

Signed and Sealed this

Twenty-second Day of December, 1998

Attest:

BRUCE LEHMAN

Attesting Officer

Commissioner of Patents and Trademarks